US007643611B2

(12) United States Patent
Shedlock et al.

(10) Patent No.: US 7,643,611 B2
(45) Date of Patent: Jan. 5, 2010

(54) METHOD AND APPARATUS FOR SHADOW APERTURE BACKSCATTER RADIOGRAPHY (SABR) SYSTEM AND PROTOCOL

(75) Inventors: Daniel Shedlock, Knoxville, TN (US); Alan M. Jacobs, Gainesville, FL (US); Sharon Auerback Jacobs, Gainesville, FL (US); Edward Dugan, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 100 days.

(21) Appl. No.: 12/112,892

(22) Filed: Apr. 30, 2008

(65) Prior Publication Data

US 2008/0285715 A1 Nov. 20, 2008

Related U.S. Application Data

(60) Provisional application No. 60/926,959, filed on Apr. 30, 2007.

(51) Int. Cl.
*G01N 23/203* (2006.01)
(52) U.S. Cl. ...................................... 378/87
(58) Field of Classification Search ............... 378/86, 378/87, 88, 89, 90
See application file for complete search history.

(56) References Cited

U.S. PATENT DOCUMENTS 5,181,234 A * 1/1993 Smith ........................ 378/87
5,940,468 A * 8/1999 Huang et al. ................. 378/57
6,735,279 B1   5/2004 Jacobs et al.
6,785,360 B1 * 8/2004 Annis ......................... 378/137
7,130,374 B1  10/2006 Jacobs et al.
7,224,772 B2   5/2007 Jacobs et al.
2008/0095298 A1 * 4/2008 Shefsky ........................ 378/2

OTHER PUBLICATIONS

Jacobs, A. M., et al., "Detection/Identification of Land Mines by Lateral Migration Radiography," *Detection of Abandoned Land Mines*, Conference Publication No. 458 IEE, Oct. 12-14, 1998, London, UK.

* cited by examiner

*Primary Examiner*—Allen C. Ho
(74) *Attorney, Agent, or Firm*—Saliwanchik, Lloyd & Saliwanchik (57) ABSTRACT

A shadow aperture backscatter radiography (SABR) system includes at least one penetrating radiation source for providing a penetrating radiation field, and at least one partially transmissive radiation detector, wherein the partially transmissive radiation detector is interposed between an object region to be interrogated and the radiation source. The partially transmissive radiation detector transmits a portion of the illumination radiation field. A shadow aperture having a plurality of radiation attenuating regions having apertures therebetween is disposed between the radiation source and the detector. The apertures provide illumination regions for the illumination radiation field to reach the object region, wherein backscattered radiation from the object is detected and generates an image by the detector in regions of the detector that are shadowed by the radiation attenuation regions.

26 Claims, 10 Drawing Sheets

FIG. 1

(PRIOR ART)

FIG. 2

(PRIOR ART)

FIG. 3

(PRIOR ART)

METHOD AND APPARATUS FOR SHADOW APERTURE BACKSCATTER RADIOGRAPHY (SABR) SYSTEM AND PROTOCOL

CROSS-REFERENCE TO RELATED APPLICATION

The present application claims the benefit of U.S. Application Ser. No. 60/926,959, filed Apr. 30, 2007, which is hereby incorporated by reference herein in its entirety, including any figures, tables, or drawings.

The subject invention was made with government support under a research project supported by NASA Contract No. NNL05AF19P. The government has certain rights in this invention.

FIELD OF THE INVENTION

The invention relates to radiography, and more particularly to radiography systems which combine aspects of both transmission and backscatter radiography, and methods thereof.

BACKGROUND OF THE INVENTION

In many industrial, military, security or medical applications, images of the internal structure of objects are required. Radiography is often used for imaging. Radiography generally comprises either conventional transmission radiography or backscatter radiography.

Figure 1:
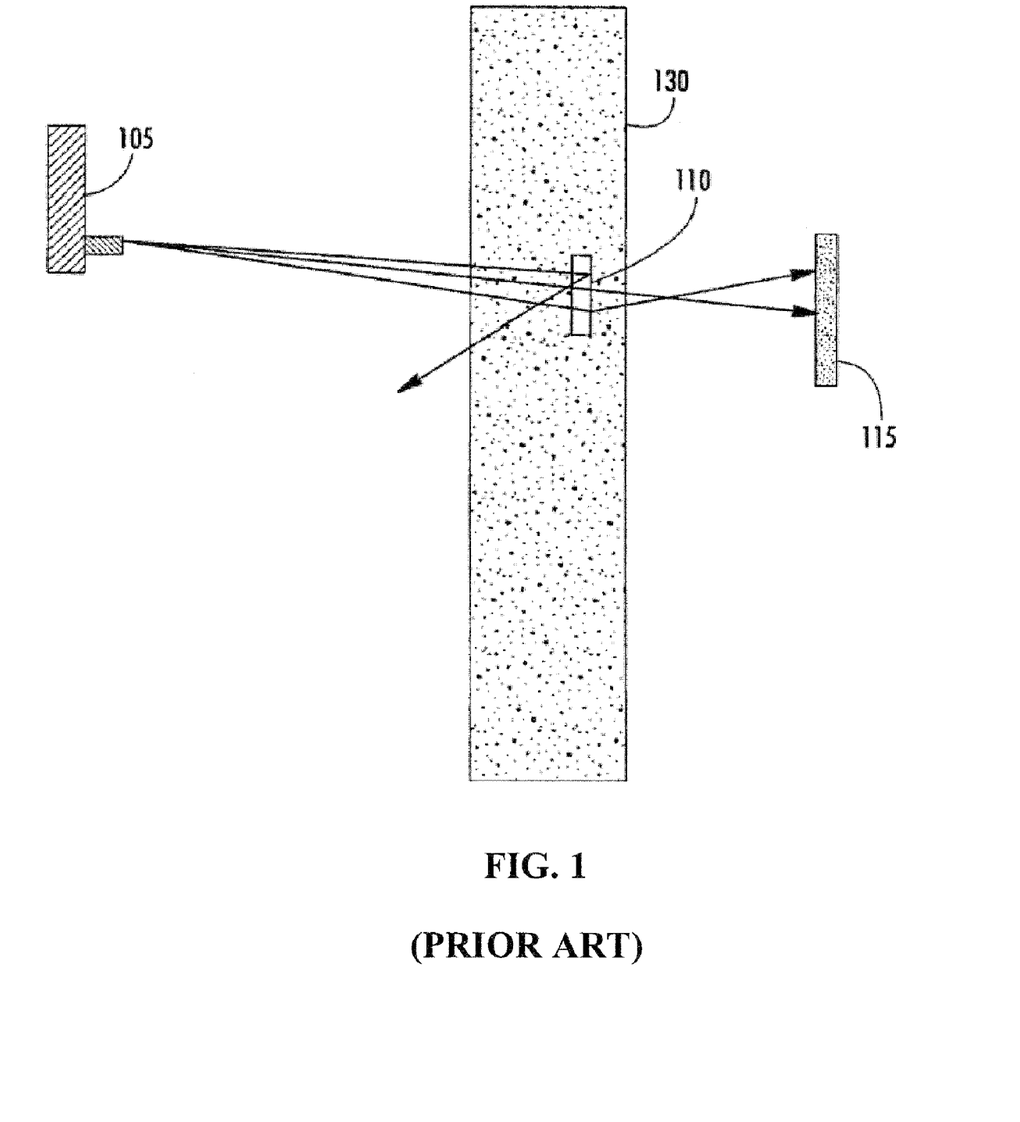
FIG. 1 is a schematic illustrating the configuration used for conventional transmission radiography.

FIG. 1 is a schematic illustrating the configuration used for conventional transmission radiography. In conventional radiography, an image is formed by transmitting radiation from a radiation generator 105 through an internal detail 110 within object 130. Attenuated radiation is received by a radiation detector 115 which is disposed on the side of the object opposite to that of the radiation generator 105. In the case of tomography, the object 130 is generally rotated about axis perpendicular to the plane of the figure.

Figure 2:
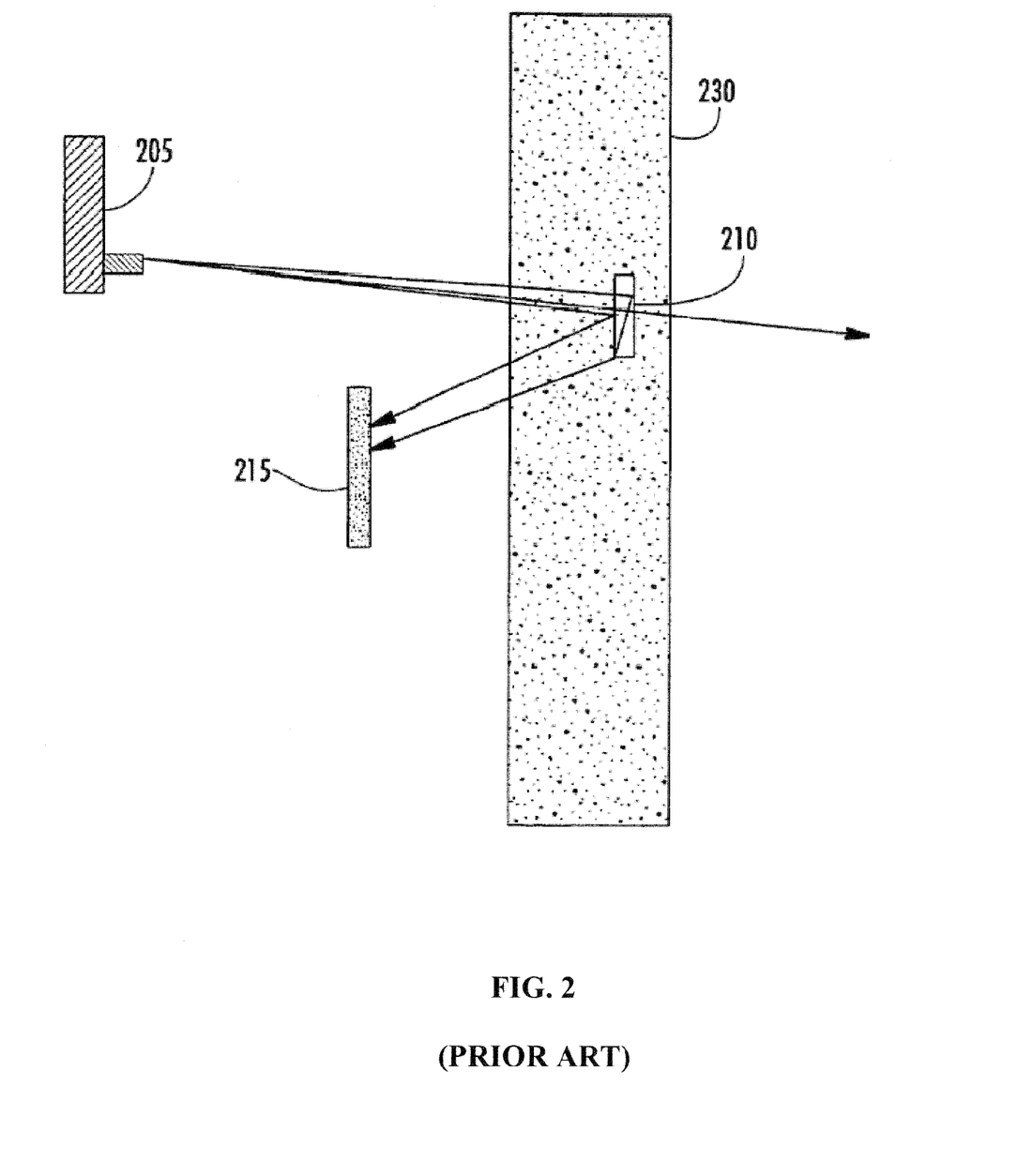
FIG. 2 is a schematic illustrating the configuration used for conventional backscatter radiography.

FIG. 2 is a schematic illustrating the configuration used for backscatter radiography. Unlike conventional radiography which relies on transmission, in backscatter radiography radiation is scattered by internal detail 210 within object 230. In backscatter radiography, the radiation generator 205 and radiation detector 215 are on the same side of the object 230. All backscatter radiography techniques allow one-sided imaging of the object since the radiation generator 205 and the radiation detector 215 are located on the same side of the object 230. This is the same imaging configuration that people and animals use for optical viewing of their surroundings. In backscatter radiography, illumination of an entire region of the object to be interrogated in a single exposure has generally only been possible using a pinhole, coded aperture, or a restriction positioned between the object and the radiation detector. This generally results in either extremely inefficient sensing of the radiation or the introduction of substantial image-obscuring structured noise, thus requiring large exposure times for typical radiation sources. An alternative includes use of a scanning pencil or fan beam for illuminating a temporal sequence of points or lines on the object surface. This also yields long exposure times and decoding algorithms having long calculation times, besides requiring an expensive scanning apparatus.

U.S. Pat. No. 6,735,279 to Jacobs et al. discloses a snapshot backscatter radiography (SBR) system and related method that includes at least one penetrating radiation source, and at least one substantially transmissive radiation detector. The substantially transmissive radiation detector is interposed between an object region to be interrogated and the radiation source. The substantially transmissive radiation detector receives and detects illumination radiation from the radiation source before transmitting a portion thereof to interrogate the object region, wherein a portion of backscattered radiation provided by the object region is detected by the detector. An image of the object can be obtained by subtracting the illumination radiation detected at the detector, or an estimate thereof, from a total of all radiation detected by the detector. U.S. Pat. No. 7,130,374 to Jacobs, et al. is based on the SBR system disclosed in U.S. Pat. No. 6,735,279 to Jacobs et al., but further discloses a changeable collimating grid having a plurality of spaced apart radiation absorbing features coupled to a structure changing a position of the plurality of features disposed in at least one of the paths of the illumination radiation and the path of the backscattered radiation.

Figure 3:
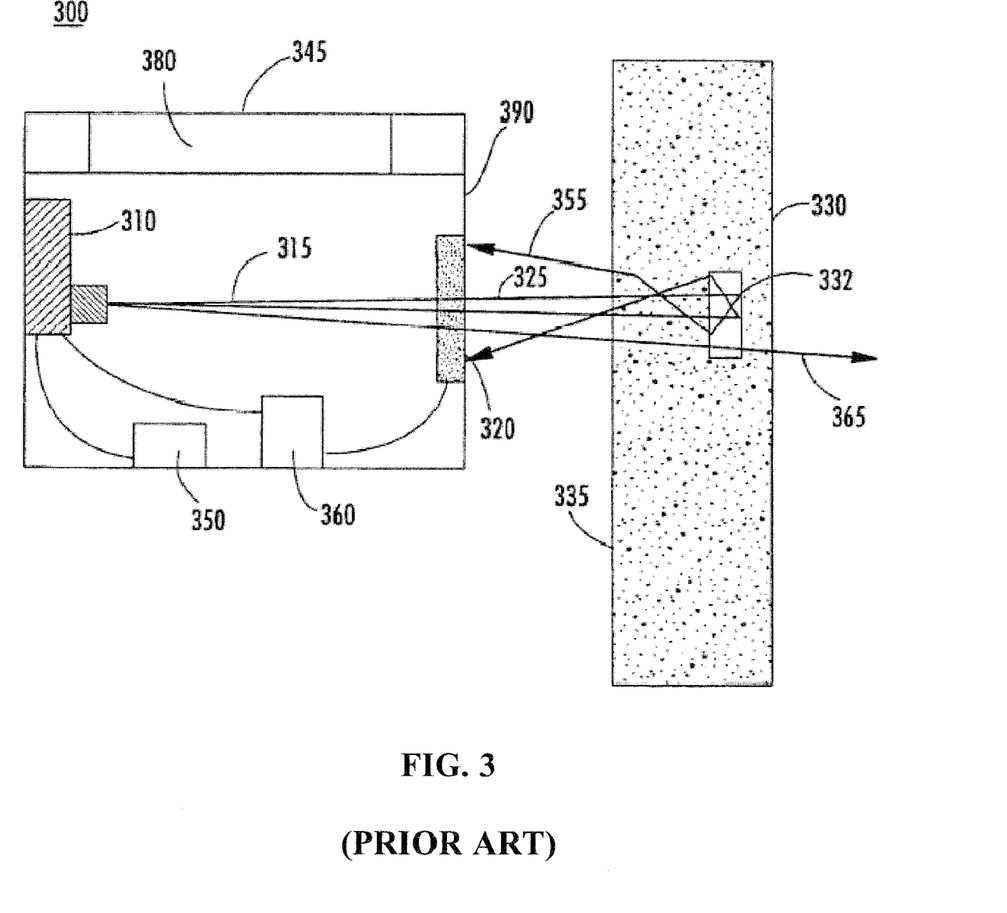
FIG. 3 is a schematic illustrating a configuration used for snapshot backscatter radiography (SBR).

FIG. 3 is a schematic illustrating a SBR system as disclosed in U.S. Pat. No. 6,735,279 to Jacobs et al. A snapshot backscatter radiography (SBR) system 300 includes at least one penetrating radiation source 310 and at least one substantially transmissive radiation detector 320, such as a flexible detector sheet. Both the radiation source 310 and the radiation detector 320 are disposed on the same side of the object 330, which includes internal detail 332. The surface of the object or the surface of the medium covering the object, such as the earth, is indicated as reference 335.

System 300 can include a radiation source controller 350 and computer 360. Computer 360 preferably includes memory and provides various system functions, such as producing data representing an image of the object interrogated based on radiation data detected by detector 320. A display screen 380 for representing an image of the object interrogated is also preferably provided.

The substantially transmissive radiation detector 320 is preferably a digitizing radiation detector-film screen. In this embodiment, computer 360 has at least modest speed and data storage capacity for data processing and driving a high resolution display 380.

Two-dimensional (2D) or three-dimensional (3D) data sufficient to generate an image of the internal structure of objects capable of scattering a portion of incident radiation is acquired in a single exposure illumination of an interrogated area of the object surface. Image data for 2D back-projections can be acquired in a single radiation generator/source burst.

System 300 is generally contained in a protective and supportive housing 345. Housing 345 holds the various components of system 300 in place.

The spacing of detector 320 from source 310 generally depends on the area to be illuminated. For most wide area applications, the spacing from source 310 to detector 320 is generally about the same order of magnitude as the length of detector 320.

The arrangement shown in FIG. 3 implies that the radiation/object interactions of primary consequence are scatterings, although absorption can also be significant. Radiation from the radiation source 310, shown by reference 315, is directed at detector 320 which detects illumination radiation 315. This detected radiation pattern is referred to as the illumination signal. The detected illumination signal includes information on the spatial variations of the illumination radiation field and the spatial variation of structure and sensitivity of the detector 320.

The substantially transmissive radiation detector 320 transmits a portion of the illumination radiation received, shown as reference 325, which penetrates surface 335 and strikes internal detail 332 of object 330. The detector medium is generally a detector sheet that provides an area that is at least equal to the illumination area provided by radiation source 310.

The internal detail 332 of object 330 then backscatters a portion of the transmitted radiation 325, shown as reference 355. Preferably, object 330 scatters (backscatters via single or multiple collisions) at least 5% to 30% of the illuminating field provided by radiation source 310. For example, a portion of radiation 325 is transmitted through object 330 and is identified in FIG. 3 as transmitted radiation 365. Substantially transmissive radiation detector 320 detects some of the backscattered radiation portion 355, the backscattered radiation pattern referred to herein as the backscatter signal. Thus, the backscatter signal is generated by the backscattered radiation field 355 that emerges from the object or other surface 335 after being scattered by the internal structure of object 330. The desired image of the object can be computed by subtracting the illumination signal, or an estimate thereof, from the total detector response measured. The total detector response measured comprises a superimposed sum of the illumination signal and the backscatter signal radiation, which includes information on the spatial variations of the radiation field and structure of the detector as well as information on the object structure. Alternatively, the desired image can be obtained by subtracting a suitably normalized incident (illumination) radiation signal, or estimate thereof, from the backscatter signal collected by the detector.

Although SBR provides advantages over conventional transmission or backscatter radiography, in SBR only a small fraction of the detection dynamic-range is employed in the algebraic formation of the backscatter image because the backscatter signal is superimposed on the illumination signal. As a result, significant image processing is required to form an image, and images can have significant feature obscuring noise.

BRIEF SUMMARY

Embodiments of the invention relate to a method and apparatus for backscatter radiography. In a specific embodiment, a shadow aperture backscatter radiography (SABR) system includes at least one penetrating radiation source for providing a penetrating radiation field, and at least one partially transmissive radiation detector, wherein the radiation detector is interposed between an object region to be interrogated and the radiation source. The radiation detector thus transmits a portion of the illumination radiation field. A shadow aperture having a plurality of radiation attenuating regions (where attenuation includes both absorption and scattering) and illumination apertures therebetween is disposed between the radiation source and the detector. The radiation attenuating regions can also be referred to as shadow regions. The apertures provide illumination regions for the illuminating radiation field to reach the object region, wherein backscattered radiation from the object is detected by the detector in regions of the detector that are shadowed from the illumination radiation by the attenuation regions of the shadow aperture.

As used herein, "partially transmissive detector" refers to a detector that transmits a portion of the illumination radiation field sufficient to form an image of an object or region of interest. Lower detector transmission results in longer exposure time, but does not generally adversely impact image quality. In one embodiment, the detector transmits at least 10% of the illumination radiation, such as at least 40% of the illumination radiation.

The shadow aperture can incorporate a mechanized shadow aperture, where open regions of the shadow aperture provide the illumination paths and the closed regions provide the radiation attenuating shadow regions. In one embodiment, the shadow aperture is disposed on the detector. In another embodiment, the shadow aperture is spaced apart from the detector.

A variety of detectors can be used with the invention. In various embodiments, the detector can include any detector medium capable of rendering a radiographic-like image. For example, the detector can be a detector including, but not limited to, a digitizing field screen, a photostimulable phosphorous-based image plate, a TFT-based flat panel detector, an amorphous silicon panel, or a CMOS array. In one embodiment, the detector can be a collimated detector, where the collimator portion is positioned between the detector and the object region. In one implementation, the system further includes a computer or processor for receiving radiation data from the detector and for performing data and image processing.

A shadow aperture backscatter radiography (SABR) method for imaging objects can include providing a shadow aperture having a plurality of radiation attenuating regions have apertures therebetween, where the apertures provide illumination regions for a radiation field to reach an object region to be interrogated. Penetrating illumination radiation is directed at the shadow aperture, where the illumination radiation incident at the apertures reaches and is transmitted by a partially transmissive radiation detector to an object region to be interrogated. The object region generates backscattered radiation that is detected by the detector in regions of the detector that are shadowed by the radiation attenuating regions. A first image is then formed from the backscattered radiation. The first image can be obtained exclusive of image processing. The method can further include displacing the shadow aperture relative to the radiation field and the detector to now shadow the illumination regions associated with the first image, and repeating the directing and forming steps, where a second image provides image data from the object region corresponding to the illumination regions in the first image. The first and second exposures can be combined into a single image.

The shadow aperture can include a mechanized shadow aperture where open regions of the shadow aperture provide the illumination paths and the closed regions provide the radiation attenuating shadow regions where the image is formed. The directing illumination step can comprise multiple exposures at varying radiation energy, where the method further includes forming a 3-D image of the object region.

BRIEF DESCRIPTION OF THE DRAWINGS

A fuller understanding of the present invention and the features and benefits thereof will be accomplished upon review of the following detailed description together with the accompanying drawings, in which.

DETAILED DISCLOSURE

Embodiments of the invention relate to a method and apparatus for backscatter radiography. In a specific embodiment, a shadow aperture backscatter radiography (SABR) system includes at least one penetrating radiation source for providing a penetrating radiation field, and at least one partially transmissive radiation detector, where the at least one partially transmissive radiation detector is interposed between an object region to be interrogated and the radiation source. The radiation detector transmits a portion of the illumination radiation field that is incident on the radiation detector. A shadow aperture having a plurality of radiation attenuation regions and illumination apertures therebetween can be disposed between the radiation source and the detector. The apertures provide illumination regions for the illuminating radiation field to reach the object region. Backscattered radiation from the object can be detected by the detector in regions of the detector that are shadowed from the illumination radiation by the attenuation regions of the shadow aperture.

Two-dimensional image data of the internal structure of an object can be acquired in a single exposure of an interrogated area of the object surface. The radiation source, shadow aperture, and image data detector are on the same side of the object, thereby defining the radiation-object interactions of primary consequence being scatterings. In embodiments of the subject SABR method and system, the temporal history of the radiation particles can be source generation/illumination spatial pattern formation by transmission through a shadow aperture/object illumination by transmission through a portion of the image detector/interaction with the object internal structure/backscatter image formation of the object internal structure by radiation-detector interaction in the areas of the detector shadowed by the attenuating regions of the shadow aperture. In comparison, all existing transmission radiography approaches are generally based on the radiation history sequence: generation/interaction with object/image formation by detector interaction. Only SBR, as described in the Background section, is characterized by a backscatter radiation history similar to SABR. However, SBR is characterized by a different transmission radiography sequence. As noted in the Background section, in SBR, the acquired image is the superposition of radiation-detector interactions from illumination radiation and object backscattered radiation. The desired (backscatter) image can then be obtained by subtraction of the known illumination signal from the total signal, leaving an image generated by only the backscattered signal. In contrast, in SABR according to an embodiment of the present invention, the acquired image is from detector areas that are shadowed by the attenuating regions of the shadow aperture. A SABR image is formed by components of the radiation scattered from the object that interact with the shaded detector regions.

Figure 4A:
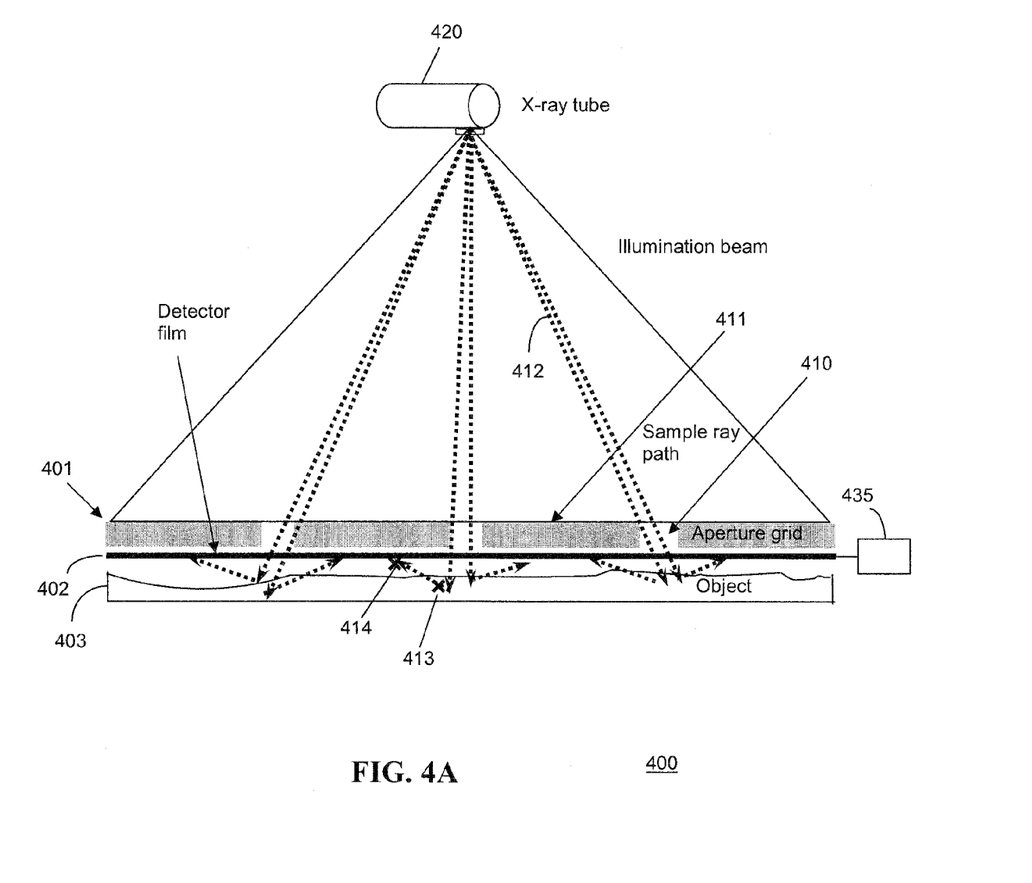
FIG. 4A is a side-view of components of a Shadow Aperture Backscatter Radiography (SABR) system according to an embodiment of the present invention illustrating typical path histories of radiation that contribute to the formation of a SABR image.

FIG. 4A shows a side-view of components of a Shadow Aperture Backscatter Radiography (SABR) system 400 according to an embodiment of the present invention. The Radiography SABR system 400 includes a radiation source. The radiation source can be an x-ray tube 420, which provides a cone shaped illumination field. It should be noted that SABR is not limited to a cone shaped illumination field. According to certain embodiments of the subject SABR system, any wide-area illumination pattern can be utilized. Referring again to FIG. 4A, the SABR system 400 can include a shadow aperture (mask) 401 having a plurality of illumination regions 410 and shadow regions 411. Shadow regions 411 can be formed of radiation attenuating materials. The detector 402 of the SABR system 400 can be positioned in front of an object region 403 to be imaged. In one embodiment, the detector 402 can be a detector film.

The purpose of the shadow aperture 401 is to inhibit the illumination field from interacting with the detector 402 in the backscatter image regions. The location of the shadow aperture 401 can remain general, but it is preferably located somewhere between the source 420 and the detector 402. In an embodiment not shown, the shadow aperture can be disposed on the detector. The backscatter image is obtained effectively only in regions of the detector 402 associated with shadowed regions 411, such as region 414. One of the many illumination paths associated with an example of backscattered radiation reaching region 414 is shown as reference 412, and the associated scatter interaction in the object region 403 is shown as reference 413. The detector 402 can be any detector medium capable of rendering a radiographic-like image or film-like x-ray image, including Polaroid® film, photography film, radiography film or any digital and/or computed radiography system.

In a further embodiment, the detector 402 can be coupled to an optional computer or processor 435, which receives radiation data from the detector 402 and performs data and image processing, such as for generating a 3-D image from a plurality of images acquired at different radiation energies.

Typically, the illumination radiation field has an associated area with bounding lines of length on the order of several inches, but depending on the source, shadow aperture, detector, and object relative geometry, the field can easily be extended to several feet. The illumination field generated by the radiation source 420 illuminates the entire area to be imaged. Because the illumination apertures 410 are small with respect to the entire illumination field, the amount of scatter radiation that is lost back-tracking (via scatter) through the aperture is generally very small with respect to the scatter components forming the image.

As shown in FIG. 4A, the angle at which the illumination field passes through the aperture 410 increases with respect to the direction normal to the detector 402. The angle relative to the surface normal should preferably be limited. When the radiation from the radiation source spreads out in the cone shape shown, the cone shape generally limits angles for the illumination beam for practical embodiments of the SABR application according to the invention to be similar to the amount of parallax that could be tolerated for transmission radiography. Although the amount of the parallax-like effect that can be tolerated is known to be generally interrogation object dependent, in a preferred embodiment the illumination beam is no more than 25 degrees off normal with the other system components, such as the detector and shadow aperture. In a more preferred embodiment, the illumination beam is no more than 20 degrees off normal.

Figure 4B:
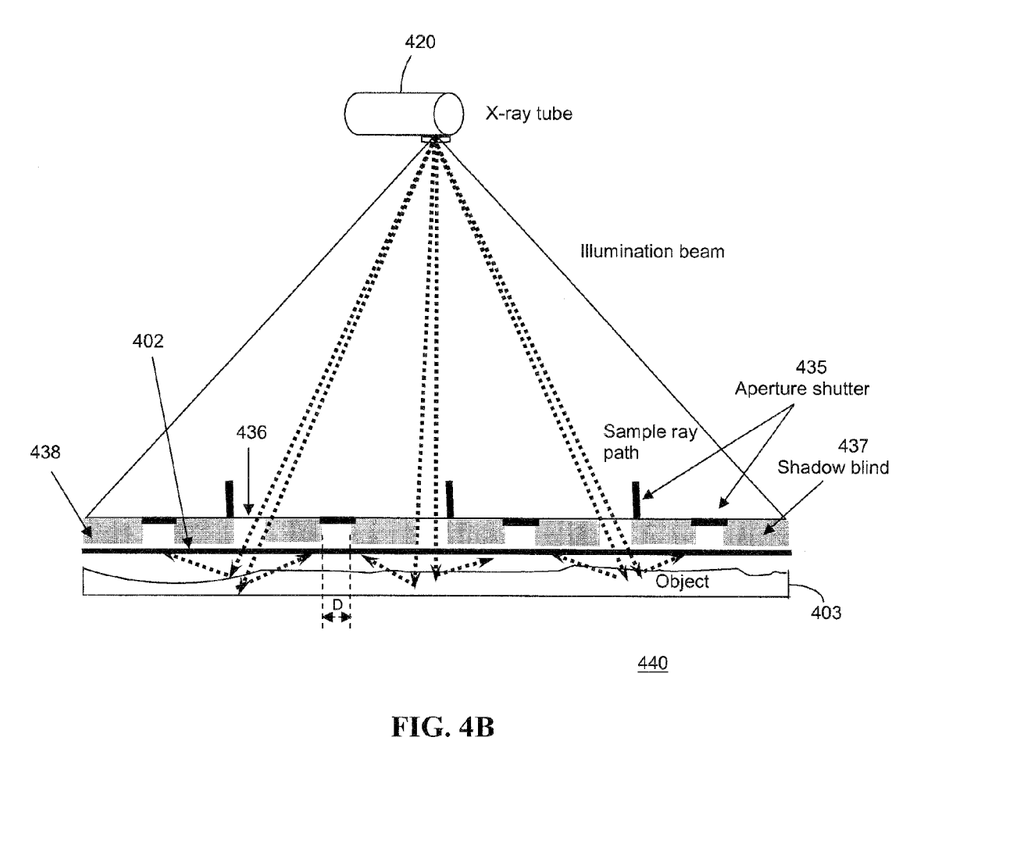
FIG. 4B shows a shadow aperture design according to an embodiment of the present invention, where open regions provide the illumination apertures and closed regions provide attenuation for the shadow regions.
Figure 4C:
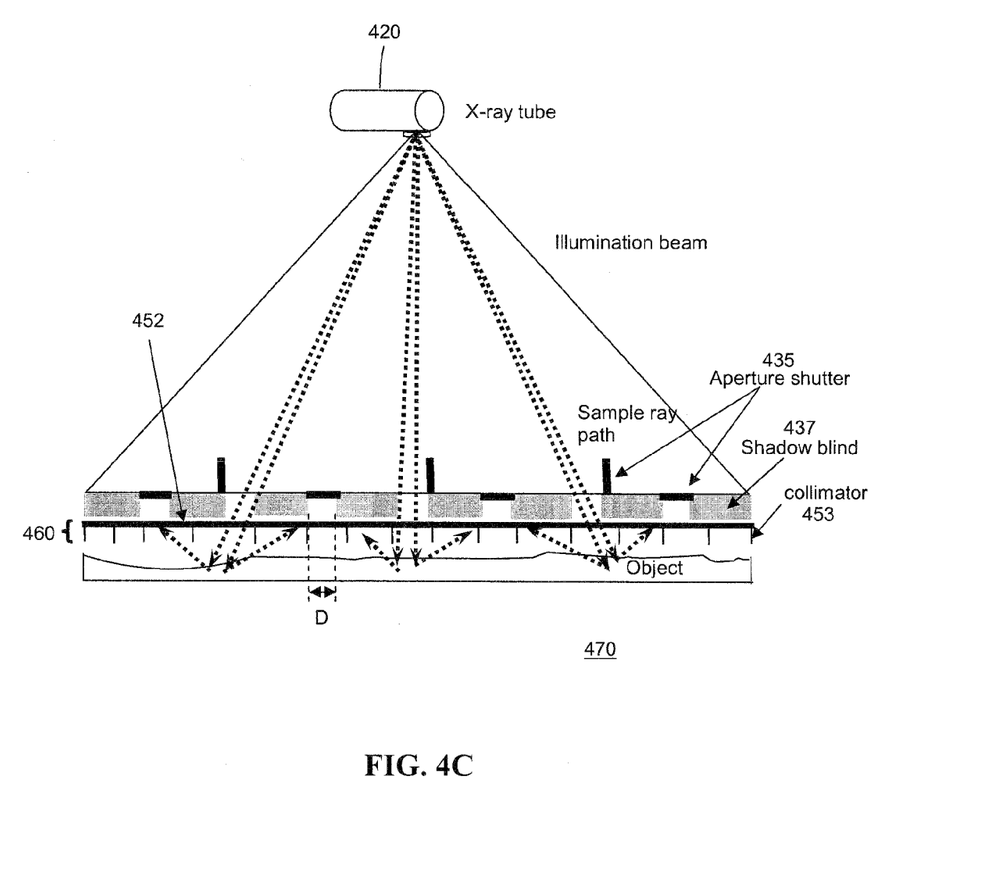
FIG. 4C shows a collimated detector that can be substituted for detector 402 shown as part of system 400 in FIG. 4(a).

The backscatter image provided by SABR according to an embodiment of the invention is effectively the same as a transmission image, except it is generated by scatter sources from the interrogation object. Scattered radiation may arrive at the detector from different angles and from different depths. This tends to cause blurring in the images and is a reason the SABR method generally provides best image quality for near surface applications. A near surface application implies a depth on the order of the illumination radiation's mean free path (mfp) in the object. Collimation between the detector 402 and interrogation object 403 can reduce this problem by limiting scatter angle and depth, such as shown in FIG. 4C.

Referring first to FIG. 4A, reference number 413 identifies one of the many detector interactions that provide the backscatter image. There are many such paths occurring simultaneously and contiguously over the entire shadow aperture (illumination apertures and shadow regions) in a single exposure. Because the backscatter signal and associated image is not available in the small illumination area (the image is only generated in the shadow regions), a second independent exposure may be desired to capture a backscatter signal in the first exposure illumination area. For the second independent exposure, the relative geometry of the source 420, shadow aperture 411, detector 402, or object 403 can be changed to capture the backscatter image not available in the first exposure. In one embodiment, this can be accomplished by moving the relative position of any of the components, such that the area of the object in the illumination area in the first exposure is in a backscatter image region in the second exposure. In another embodiment, this can be accomplished by means of a mechanized shadow aperture 438 that moves the location of the illumination field, as shown in FIG. 4B, and then taking a second (independent) exposure. It is then possible to stitch the two independent exposures together to make a single image. Additional images can also be taken and stitched in as well.

In an embodiment, the size of the shadow regions 411 (or separation of the illumination apertures) can be on the order of about two mean-free-paths for the radiation in the object material. In specific embodiments, the separation of the illumination aperture is less than three mean-free paths and less than two mean-free paths, respectively. For example, the mean free path is about 1 cm in aluminum and 5 to 6 cm in nylon for 50 keV x-rays. The aperture areas 410 in such an embodiment could be about 1 mm in width, thus for the aluminum example being about ½₀ the size of the shadow regions.

As clearly shown in FIG. 4A, in SABR the image is effectively acquired only from detector areas that are shadowed near the aperture and is thus formed by portions of the illumination field that pass through the aperture, scatter from the object, and then interact with the aperture shaded detector regions.

FIG. 4B shows a system 440 including a shadow aperture embodied using a mechanized shadow aperture 438. Open regions in the shadow aperture 438 are identified as illumination apertures 436, which correspond to locations where aperture shutters 435 are "open" to provide the illumination region. Attenuation regions correspond to locations of fixed shadow blinds 437 and locations where the aperture shutters 435 are "closed," and provide the shadow region. The aperture shutters 435 and the shadow blinds 437 can be integrated as shown. In the embodiment shown, the mechanized shadow aperture 438 incorporates a set of offset rotating aperture shutters 435 providing a pattern of shadow apertures and illumination apertures. The aperture shutters 435 can be hinged shutters. One example embodiment for a uniform shadow aperture grid can include mechanized apertures 436 spaced equidistant apart, where the apertures 436 can each have a width D. In the embodiment shown in FIG. 4B, every other mechanized aperture shutter 435 is oriented perpendicular (open) to the detector-plane and the remaining mechanized aperture shutters are parallel (closed) to the detector-plane. However, implementations are not limited thereto. In operation, this set of open and closed apertures 436 are placed between the radiation source and the detector, and will function as a shadow aperture array. This is only one example of how the images can be obtained. Although shown with uniform width D, the illumination apertures do not need to be of uniform width or uniform spacing and may be fitted to a shadow aperture pattern, such as the shadow aperture pattern shown in FIG. 5.

FIG. 4C shows a system 470 including a collimated detector 460 having the combination of detector 452 and collimator 453, the combination which can be substituted for the detector 402 shown as part of system 400 in FIG. 4A. Collimation between the detector and interrogation object can reduce image blurring caused by scattered particles being detected that come from a wide range of different angles. Although not shown, the collimators can be dynamically adjustable, such as disclosed in U.S. Pat. No. 7,130,374 to Jacobs, et al., which is hereby incorporated by reference in its entirety.

Figure 5:
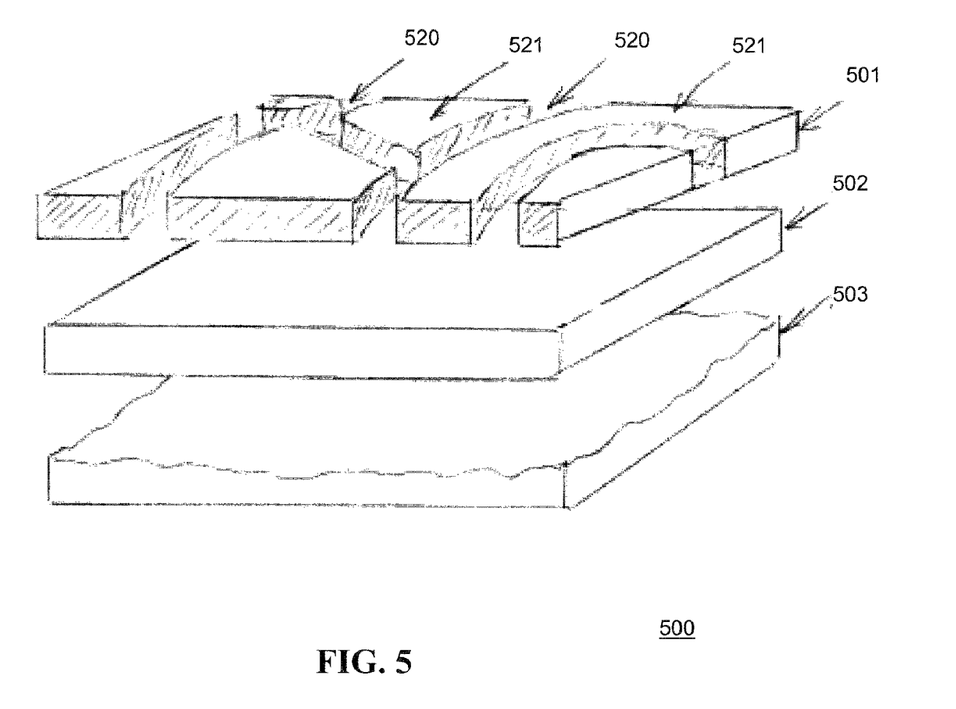
FIG. 5 is an isometric-view of an embodiment of an SABR system illustrating an exemplary shadow aperture pattern.

FIG. 5 is an isometric-view of an embodiment of a SABR system 500 illustrating an exemplary shadow aperture pattern. The shadow aperture 501 has illumination regions 520 and shadow regions 521. The detector is identified with reference 502, and reference 503 identifies the object to be imaged.

Penetrating radiation that can be used with the present invention includes, but is not limited to, x-rays, gamma rays, or neutrons.

The detector can be selected to permit a portion of the illumination radiation to be transmitted therethrough sufficient to form an image. In one embodiment the detector can be selected to permit at least 40% of the illumination radiation to transmit therethrough. In a preferred embodiment, the detector can be selected to permit 60% to 80%, or more of the illumination radiation to transmit therethrough. There are many x-ray imaging detector technologies that can be used with the SABR approach according to the present invention. Any media capable of rendering an x-ray image with transmissive properties can be used. This includes but is not limited to photography film, Polaroid® film, radiography film, a photostimulable phosphor-based image plate (commonly referred to as computed radiography (CR)), an amorphous silicon panel (ASP) conversion screen bonded to an array of photosensitive diodes, or any other type of digital radiography (DR) media such as CMOS detector arrays that can be configured to allow partial transmission of the illumination source. The generic use of "detector" implies any one of these x-ray media.

The CR imaging medium is generally thin, uniform, and flexible. X-ray sensitivity and image spatial resolution are sufficient for most applications. Significant care should be exercised in the time between latent image acquisition and photo stimulation in the image reading process including light exclusion. As the technique is conventionally applied, there is a separate image reader device and the imaging plate (film) is transferred from the x-ray illumination device to the reader for image digitizing and display. For application of the CR method to a SABR system, it would be advantageous if image exposure, reading, digitization, and display were accomplished in the same device in order to eliminate the physical transfer of the imaging plate in the process.

Most ASP detectors are neither thin nor homogeneous, but there are panel models where the associated amplifiers and voltage supplies are placed to the side of the imaging area. Typical panels are heavily shielded against x-ray penetration from the rear, which tends to negate the geometric necessities of the SABR system. However, custom panels can be produced to allow illumination passage.

A major advantage of an ASP and CMOS detector arrays is the inherent, single-step image acquisition process. Data from a sequence of images can be acquired and stored for processing. Image data obtained from a series of varying x-ray generator voltages can be employed to yield 3D images of internal structure. Image data obtained from a series of x-ray generator pulses can also form the basis of analysis of the dynamic response of internal structure, such as suggested in the development of dynamic radiography (Kenney & Jacobs, Research Techniques in Nondestructive Testing, Chapter 6, pp. 217-243, Edited by Sharpe, Academic Press, 1977). With sufficient temporal resolution of the panel, a single x-ray generator pulse with time-varying spectrum can be employed to efficiently acquire data for either of these applications.

CCD or other chip-based detectors may also be used in applications where a large area image is not required. Chip based detectors are generally useful when the area to be interrogated is relatively small, such as on the order of several micrometers, tens of micrometers, or hundreds of micrometers, such as a region on an integrated circuit. Thin film transistor arrays (TFT-arrays) may also be used with embodiments of the invention.

Benefits from embodiments of the present invention are several and significant. The equivalent of an optical snapshot camera is often desirable, but has heretofore been generally available only for conventional projection (transmission) radiography. Embodiments of the invention allow snapshot exposure radiography utilizing backscattered, rather than transmitted, radiation. The compact size, absence of mechanical mechanisms, and small time increment for image acquisition, contribute to efficiency, accuracy, and viability of many diagnostic and/or process-control applications. In contrast to the related SBR approach, embodiments of the invention allow such benefits using the full dynamic-range of the detector. This provides far greater image contrast and far lower image noise with much less, and even zero, image data manipulation.

Embodiments of the present invention can be used in a variety of products. Obtaining images of internal structure, or defects, of objects is an important diagnostic tool in many industrial, military, security, and medical situations, particularly in cases in which there is only one-sided access to the object and for which slow and expensive image acquisition is inappropriate. Other applications include situations wherein a near-surface (within approximately one radiation mean-free-path of the object surface) structure element, or defect, is difficult or impossible to image by conventional projection radiography. Moreover, all orders of scatter and transport thereby implied (i.e., radiography by selective detection (RSD) and lateral migration radiography (LMR)) utilized to produce a backscatter image can be implemented through embodiments of the subject SABR approach. RSD and LMR radiation path histories can enhance image contrast of sub-surface features that are obscured in other radiography techniques. Radiography applications, wherein internal structures, or defects, are to be imaged, benefit significantly from the backscatter point of view of SABR. This approach makes such examinations quick and inexpensive.

A clear benefit of the SABR approach is for radiography applications in which there is only one-sided access to the object. For example, scanning electron microscopes (SEM) are commonly used in integrated circuit failure analysis and some process control that require resolution beyond that provided by standard optical inspections. One reason for common use of SEMs in integrated circuit processing is because of its high image resolution compared to standard optical inspection tools. Moreover, transmission radiography is generally not possible for interrogating integrated circuits due to the presence of one or more heavily absorptive surfaces. For example, gold may coat the backside of the chip. Significantly, unlike SABR systems that can interrogate below the surface of a sample, conventional SEMs cannot interrogate regions below the surface. In addition, SABR systems are expected to be inexpensive relative to SEMs. As noted above, the SABR system can provide improved image resolution, and provide a resolution comparable to that obtainable from conventional SEMs by including one or more collimator systems to reduce the beam size as required for the desired resolution level.

Embodiments of the present invention are also helpful where an internal structure element is difficult or impossible to image by conventional transmission radiography or even conventional backscatter radiography because of the ability to take advantage of enhanced image contrast during the subsurface scatter through the use of collimation. Accordingly, the present invention can be applied to Radiography by selective detection (RSD) described in U.S. Pat. No. 7,224, 772 to Jacobs et al., which is hereby incorporated by reference in its entirety. RSD is an enhanced single-side x-ray Compton backscatter imaging (CBI) technique which selectively detects scatter components to improve image contrast and quality. Scatter component selection is accomplished through a set of specially designed detectors with fixed and movable collimators. Adjustments to the adjustable collimator selects particular directions of travel of scattered radiation emitted from an irradiated object that reach the detector. The collimated detector is preferably a collimated detector array, where the collimators are independently adjustable. The independent motion capability provides the capability to focus the image by selection of the desired scatter field components. When an array of reconfigurable collimated detectors is provided, separate image data can be obtained from each of the detectors and the respective images cross-correlated and combined to form an enhanced image.

Embodiments of the invention can be applied to a variety of applications as they enable rapid large area, side-sided x-ray exposures that generates radiographic images of an object or volume of interest and can also be incorporated into a portable system. For example, applications can include non-destructive evaluation (NDE) of aluminum, carbon composites, and any low density material with favorable scattering-to-absorption cross sections used in industrial applications.

Embodiments of the system can be small and lightweight, making the system readily mobile.

EXAMPLE

The present invention is further illustrated by the following example. This example is provided for illustration only and is not to be construed as limiting the scope or content of the invention in any way.

Figure 6:
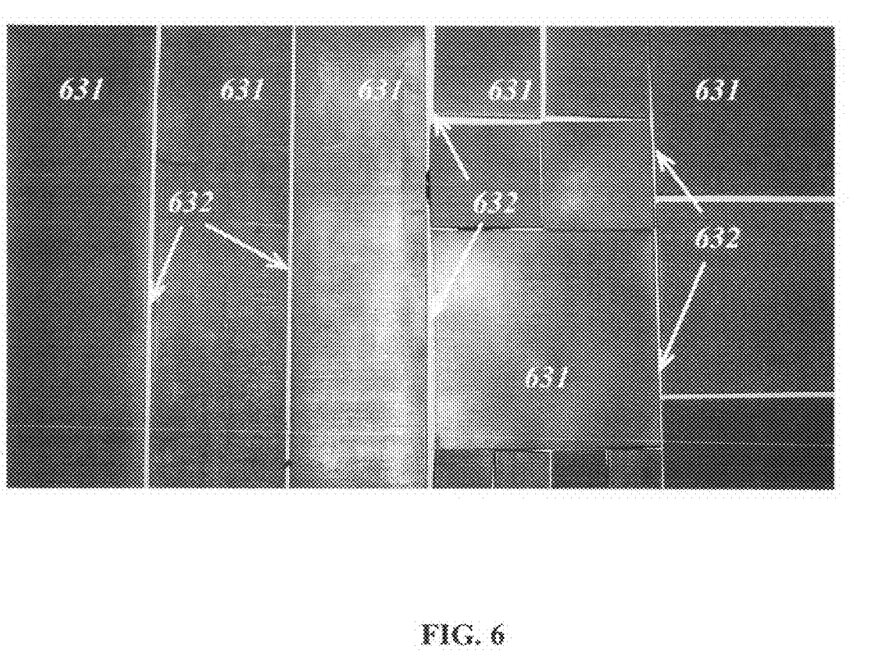
FIG. 6 is a photograph of an exemplary shadow aperture employed in experiments performed.
Figure 7:
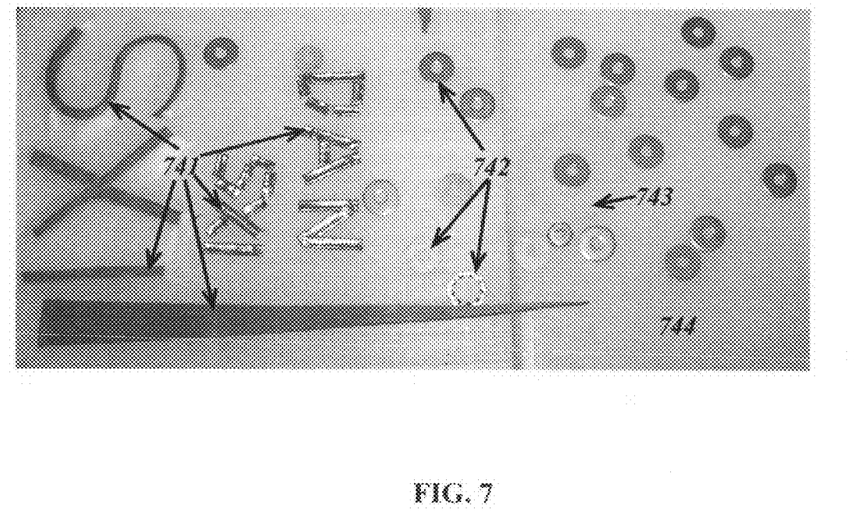
FIG. 7 is a photograph of an object array used to test an SABR system according to an embodiment of the present invention.
Figure 8:
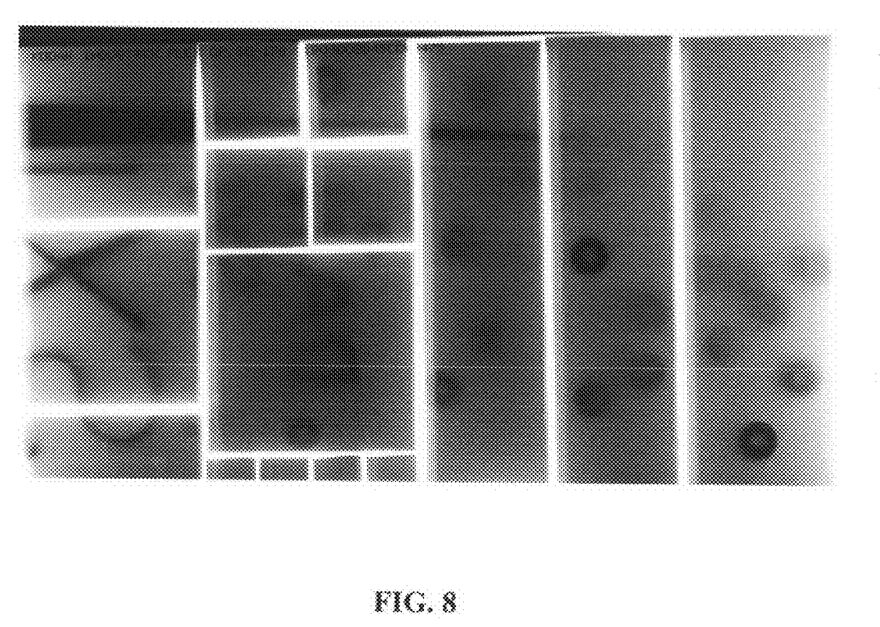
FIG. 8 is an x-ray SABR image of the object array shown in FIG. 7 using the shadow aperture shown in FIG. 6, where the image shown was obtained without any attempt of optimization of the shadow aperture geometry or the x-ray exposure parameters.

FIG. 6 is a photograph of an exemplary shadow aperture used for the present example. 631 are shadow regions made of lead sheeting. 632 are illumination regions which are the uncovered areas of a sheet of paper on which the lead shadow region sheets are glued. FIG. 7 is a photograph of an object array used to test the SABR system. Reference 741 indicates pieces of lead. Reference 742 indicates various nuts and washers made from aluminum, brass and steel. Reference 743 indicates a nylon washer. The objects are provided on a substrate 744 made from 6/6 nylon. FIG. 8 is a single exposure x-ray SABR image of the object array shown in FIG. 7 using the shadow aperture shown in FIG. 6 obtained using a CR image detector without any attempt of optimizing either the aperture or the x-ray exposure parameters. Thus, the SABR parameters, such as shadow aperture dimensions and x-ray illumination parameters, employed were chosen arbitrarily and were likely not close to the optimums for the object used. The single x-ray exposure was 70 kVp for 120 mAs. The focal spot (FOC) of the x-ray tube was located 47 inches from the surface of the film. FIG. 8 evidences the viability of the present invention. The result shown is meant to only exhibit such a demonstration. The object itself was chosen solely for ease of demonstration rather than any practical interest.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

We claim:

1. A radiography system, comprising:
   at least one penetrating radiation source for providing a penetrating radiation field;
   at least one partially transmissive radiation detector, wherein said partially transmissive radiation detector is interposed between an object region to be interrogated and the at least one penetrating radiation source, wherein the at least one partially transmissive radiation detector transmits a portion of the penetrating radiation field incident on the at least one partially transmissive radiation detector, and
   a shadow aperture comprising a plurality of radiation attenuating regions having at least one illumination aperture therebetween two or more of the plurality of radiation attenuating regions, wherein the shadow aperture is disposed between the at least one penetrating radiation source and the at least one partially transmissive detector, wherein the at least one illumination aperture allows the penetrating radiation field to reach the object region, wherein backscattered radiation from the object region is detected by the at least one partially transmissive radiation detector in shadowed regions of the at least one partially transmissive radiation detector that are shadowed by the radiation attenuating regions of the shadow aperture.

2. The system according to claim 1, wherein the shadow aperture comprises at least one shutter, wherein when one of the at least one shutter is open, the open shutter contributes to the at least one illumination aperture, and wherein when one of the at least one shutter is closed, the closed shutter contributes to the plurality of radiation attenuating regions.

3. The system according to claim 2, wherein the shadow aperture is a mechanized shadow aperture, wherein the at least one shutter is mechanized.

4. The system according to claim 1, wherein said shadow aperture is disposed on the at least one partially transmissive radiation detector.

5. The system according to claim 1, wherein said shadow aperture is spaced apart from the at least one partially transmissive radiation detector.

6. The system according to claim 1, wherein the at least one partially transmissive radiation detector comprises a detector medium capable of rendering a radiographic-like image.

7. The system according to claim 6, wherein the at least one partially transmissive radiation detector comprises a photostimulable phosphorous-based image plate.

8. The system according to claim 6, wherein the at least one partially transmissive radiation detector comprises a TFT-based flat panel detector, an amorphous silicon panel, or a CMOS array.

9. The system according to claim 1, further comprising a computer or processor for receiving radiation data from the at least one partially transmissive radiation detector and for performing data and image processing.

10. The system according to claim 1, further comprising at least one collimator positioned between the at least one partially transmissive radiation detector and the object region.

11. The system according to claim 1, wherein the at least one partially transmissive detector transmits at least 10% of radiation incident on the at least one partially transmissive detector.

12. The system according to claim 1, wherein the at least one partially transmissive detector transmits at least 40% of radiation incident on the at least one partially transmissive detector.

13. The system according to claim 1, wherein the at least one illumination aperture are spaced apart from each other by less than three mean-free paths for the penetrating radiation field in the object region.

14. A method for radiography, comprising:
    positioning a shadow aperture between an object region to be interrogated and an at least one penetrating radiation source, wherein the shadow aperture comprises a plurality of radiation attenuating regions having at least one illumination aperture therebetween two or more of the plurality of radiation attenuating regions;
    positioning at least one partially transmissive radiation detector between the shadow aperture and the object region, wherein the at least one partially transmissive radiation detector transmits a portion of the penetrating radiation field incident on the at least one partially transmissive radiation detector;
    directing a penetrating radiation field from the at least one penetrating radiation source to the shadow aperture, wherein the at least one illumination aperture allows the penetrating radiation field to reach the object region; and
    detecting backscattered radiation from the object region via shadowed regions of the partially transmissive detector shadowed by the radiation attenuating regions.

15. The method according to claim 14, further comprising producing an image from the detected backscattered radiation.

16. The method according to claim 14, further comprising displacing the shadow aperture relative to the object region such that the portion of the object region to which the penetrating radiation field reached for the first image is shadowed by the plurality of radiation attenuating regions of the shadow aperture, directing a second penetrating radiation field, detecting additional backscattered radiation from the object region, and producing a second image, wherein the second image provides image data from the object region corresponding to where the penetrating radiation field reached the object region for the first image.

17. The method according to claim 16, wherein the second penetrating radiation field has a different energy than the penetrating radiation field.

18. The method according to claim 16, further comprising combining the first image and the second image into a combined image.

19. The method according to claim 14, wherein the first image is obtained exclusive of image processing.

20. The method according to claim 14, wherein the shadow aperture comprises at least one shutter, wherein when one of the at least one shutter is open, the open shutter contributes to the at least one illumination aperture, and wherein when one of the at least one shutter is closed, the closed shutter contributes to the plurality of radiation attenuation regions.

21. The method according to claim 20, further comprising mechanically closing one or more of the at least one shutter and/or mechanically opening other of the at least one shutter;
   directing a second penetrating radiation field;
   detecting additional backscattered radiation from the object region; and
   producing a second image from the detected additional backscattered radiation, wherein the second image provides image data from the object region corresponding to where the penetrating radiation field reached the object region for the first image.

22. The method according to claim 14, further comprising:
   directing at least one additional penetrating radiation field to the shadow aperture, wherein each of the at least one additional penetrating radiation field has a different energy than each of the other at least one additional penetrating radiation field and the penetrating radiation field;
   detecting a corresponding at least one additional backscattered radiation from the object region; and
   producing a corresponding at least one additional image from the detected corresponding at least one additional backscattered radiation.

23. The method according to claim 14, wherein the at least one partially transmissive detector transmits at least 10% of radiation incident on the at least one partially transmissive detector.

24. The method according to claim 14, wherein the at least one partially transmissive detector transmits at least 40% of radiation incident on the at least one partially transmissive detector.

25. The method according to claim 14, further comprising positioning at least one collimator between the partially transmissive detector and the object region.

26. The method according to claim 14, wherein the at least one illumination aperture are space apart from each other by less than three mean-free paths for the penetrating radiation field in the object region.

* * * * *